US010179139B2

(12) United States Patent
Malhotra et al.

(10) Patent No.: US 10,179,139 B2
(45) Date of Patent: Jan. 15, 2019

(54) PHARMACEUTICAL COMPOSITION

(75) Inventors: Geena Malhotra, Mumbai (IN);
Shrinivas Madhukar Purandare,
Mumbai (IN)

(73) Assignee: CIPLA Limited, Mumbai (IN)

( * ) Notice: Subject to any disclaimer, the term of this patent is extended or adjusted under 35 U.S.C. 154(b) by 0 days.

(21) Appl. No.: 13/879,145

(22) PCT Filed: Jul. 25, 2011

(86) PCT No.: PCT/GB2011/001115
§ 371 (c)(1),
(2), (4) Date: Jul. 10, 2013

(87) PCT Pub. No.: WO2012/049444
PCT Pub. Date: Apr. 19, 2012

(65) Prior Publication Data
US 2014/0147393 A1 May 29, 2014

(30) Foreign Application Priority Data

Oct. 20, 2010 (IN) .......................... 2847/MUM/2010
Jan. 10, 2011 (IN) ............................. 69/MUM/2011
Jan. 12, 2011 (IN) ........................... 106/MUM/2011
Jan. 14, 2011 (IN) ........................... 135/MUM/2011
Jan. 17, 2011 (IN) ........................... 143/MUM/2011

(51) Int. Cl.
| A61K 31/58 | (2006.01) |
| A61K 9/00 | (2006.01) |
| A61K 31/167 | (2006.01) |
| A61K 31/46 | (2006.01) |
| A61K 31/4704 | (2006.01) |
| A61K 31/573 | (2006.01) |
| A61K 45/06 | (2006.01) |

(52) U.S. Cl.
CPC .............. *A61K 31/58* (2013.01); *A61K 9/008* (2013.01); *A61K 9/0075* (2013.01); *A61K 9/0078* (2013.01); *A61K 31/167* (2013.01); *A61K 31/46* (2013.01); *A61K 31/4704* (2013.01); *A61K 31/573* (2013.01); *A61K 45/06* (2013.01)

(58) Field of Classification Search
None
See application file for complete search history.

(56) References Cited

U.S. PATENT DOCUMENTS

| 6,120,752 A * | 9/2000 | Oliver ..................... A61K 9/008 424/45 |
| 8,048,910 B2 | 11/2011 | Maus et al. |
| 8,668,901 B2 * | 3/2014 | Muellinger .......... A61K 9/0078 128/200.13 |
| 2002/0103260 A1 * | 8/2002 | Clarke ................. A61K 9/0075 514/630 |
| 2004/0118007 A1 | 6/2004 | Chickering, III et al. |
| 2005/0287079 A1 | 12/2005 | Clarke et al. |
| 2006/0008498 A1 | 1/2006 | Chen |
| 2006/0035874 A1 * | 2/2006 | Lulla et al. ................... 514/171 |
| 2006/0110330 A1 | 5/2006 | Pieper |
| 2009/0136757 A1 | 5/2009 | Wursche et al. |
| 2009/0298802 A1 * | 12/2009 | Sequeira .............. A61K 9/0073 514/171 |
| 2010/0172994 A1 | 7/2010 | Sigmund et al. |
| 2011/0086827 A1 | 4/2011 | Weimar et al. |
| 2011/0114745 A1 | 5/2011 | Buisson et al. |
| 2013/0074834 A1 | 3/2013 | Lulla et al. |
| 2015/0098999 A1 | 4/2015 | Lulla et al. |

FOREIGN PATENT DOCUMENTS

| CN | 101321539 A | 12/2008 |
| CN | 101474191 A | 7/2009 |
| CN | 101474191 B * | 3/2011 |
| EP | 1277787 A1 | 1/2003 |
| EP | 1834624 A1 | 9/2007 |
| EP | 2143423 A1 | 1/2010 |
| EP | 2221048 A1 | 8/2010 |
| EP | 2627325 A1 | 8/2013 |
| JP | 2002537249 A | 11/2002 |
| JP | 2004514739 A | 5/2004 |
| JP | 2005523268 A | 8/2005 |
| JP | 2005539046 A | 12/2005 |
| JP | 2006514686 A | 5/2006 |
| JP | 2008520621 A | 6/2008 |
| JP | 2010519195 A | 6/2010 |
| KR | 20090121338 A | 11/2009 |
| WO | 09/11243 A1 | 3/1999 |
| WO | 2000048587 A1 | 8/2000 |
| WO | 02/45703 A2 | 6/2002 |
| WO | 03/066033 A1 | 8/2003 |

(Continued)

OTHER PUBLICATIONS

COPD (chronic obstructive pulmonary disease)—Cause, WebMD Medical Reference from Healthwise, Oct. 16, 2012.*
Tashkin (Indacaterol maleate for the treatment of chronic obstructive pulmonary disease, Expert © pin, Pharmacother (2010) 11 (12):2077-2085).*
Tashkin (Indacaterol maleate for the treatment of chronic obstructive pulmonary disease, Expert © pin, Pharmacother (201 O) 11 (12):2077-2085).*
Tashkin (Indacaterol maleate for the treatment of chronic obstructive pulmonary disease, Expert Opin, Pharmacother (2010) 11(12):2077-2085).*
"Fluticasone furoate/fluticasone propionate—different drugs with different properties"; The Clinical Respiratory Journal (2011) (Year: 2011).*
European Examination Report, Application No. EP 11752315.9 dated Feb. 23, 2015.

(Continued)

*Primary Examiner* — Robert A Wax
*Assistant Examiner* — Melissa S Mercier
(74) *Attorney, Agent, or Firm* — MacMillan, Sobanski & Todd, LLC

(57) ABSTRACT

Described herein is a pharmaceutical composition that includes a beta$_2$-agonist selected from indacaterol and formoterol in combination with a corticosteroid selected from fluticasone and ciclesonide, and, optionally, one or more pharmaceutically acceptable excipients.

11 Claims, No Drawings

(56) References Cited

FOREIGN PATENT DOCUMENTS

| WO | 2004019985 A1 | 3/2004 |
| --- | --- | --- |
| WO | 2004/110460 A1 | 12/2004 |
| WO | 2005/053851 A1 | 6/2005 |
| WO | 2008102128 A2 | 8/2008 |
| WO | 2010007446 A1 | 1/2010 |
| WO | WO 2010007446 A1 * | 1/2010 |
| WO | 2010121323 A1 | 10/2010 |
| WO | 2011048412 A1 | 4/2011 |
| WO | 2012049444 A1 | 4/2012 |

OTHER PUBLICATIONS

Chinese First Office Action, Application No. CN 2011800597356 dated Apr. 29, 2014.
Chinese Second Office Action, Application No. CN 2011800597356 dated Mar. 18, 2015.
New Zealand First Office Action, Application No. NZ 609358 dated Jan. 7, 2014.
New Zealand Second Office Action, Application No. NZ 609358 dated Jan. 26, 2015.
PCT International Preliminary Report on Patentability, Application No. PCT/GB2011/001115 dated Apr. 25, 2013.
Notification of the Third Chinese Office Action, Application No. CN 2011800597356 dated Oct. 12, 2015.
Japanese Final Office Action, Application No. JP 2013-533267, dated Jun. 7, 2016.
Russian Office Action, Application No. 2013119938, dated May 4, 2017.
Canada Office Action, Application No. 2814445, dated Oct. 17, 2017.
Indian Office Action, Application No. IN 844/MUMNP/2013, dated Feb. 2, 2018.
Korean Office Action, Application No. KR 10-2013-7012107, dated Apr. 13, 2016.
Keck et al., "Drug nanocrystals of poorly soluble drugs produced by high pressure homogenization", European Journal of Pharmaceutics and Biopharmaceutices, 2006, vol. 62, No. 1, pp. 3-16, Abstract Only.
Kesisoglou et al., "Nanosizing—Oral formulation development and biopharmaceutical evaluation", Advanced Drug Delivery Reviews, 2007, vol. 59, No. 7, pp. 631-644, Abstract Only.
European Research Report Request for Provisional Patent No. 106237 dated Oct. 10, 2014, Received Feb. 2, 2016.
Russian Office Action, Application No. 2013119938/15 dated Jan. 25, 2016.
Japanese Office Action, Application No. JP 2013-533267, dated Jul. 27, 2014.
Mexican Third Office Action, Application No. MX/a/2013/004137, dated Aug. 11, 2015.
Russian Office Action, Application No. RU 2013119938, dated Aug. 19, 2015.

* cited by examiner

PHARMACEUTICAL COMPOSITION

The present invention claims the benefit of the PCT/GB2011/001115 filed Jul. 25, 2011, which claims priority to Ser. Nos. 2847/MUM/2010 filed 12 Oct. 2010; 69/MUM/2011 filed 10 Jan. 2011; 106/MUM/2011 filed 12 Jan. 2011; 135/MUM/2011 filed 14 Jan. 2011; and, 143/MUM/2011 filed 17 Jan. 2011.

FIELD OF INVENTION

The present invention relates to pharmaceutical compositions for inhalation. There is also provided a process for preparing the compositions and use thereof in the treatment and/or prevention of respiratory, inflammatory or obstructive airway disease.

BACKGROUND OF INVENTION

Asthma is a major cause of chronic morbidity and mortality, with an estimated 300 million affected individuals worldwide and 2, 50,000 annual deaths attributed to the disease. People of all ages in most countries are affected by this chronic disease.

Asthma is a chronic inflammatory disorder of the airways associated with airway hyper responsiveness that leads to recurrent episodes of wheezing, breathlessness, chest tightness, and coughing. An increased inflammatory response is a major part of the pathophysiology of acute asthma, and regular preventive treatment is important.

Chronic obstructive pulmonary disease (COPD) is a severe respiratory condition that is increasing in prevalence worldwide. In India, the estimated prevalence is about 12.36 million. It is currently the fourth leading cause of death in the UK & US, and predicted to rank third in the global impact of disease by the year 2020.

Chronic obstructive pulmonary disease (COPD) is a preventable and treatable disease state characterized by air flow limitation that is not fully reversible. The airflow obstruction is usually progressive and associated with an abnormal inflammatory response of the lungs to noxious particles or gases, primarily caused by cigarette smoking. Although COPD affects the lungs it also produces significant systemic consequences. COPD is associated with mucus hyper secretion, emphysema, bronchiolitis.

Therapy for the treatment and/or prevention of asthma and chronic obstructive pulmonary disease (COPD) currently includes the use of bronchodilators such as $beta_2$-agonists, anticholinergics and steroids.

More specifically asthma, COPD and other related disorders have been known to be treated with $beta_2$-agonist as they provide a bronchodilator effect, resulting in relief from the symptoms of breathlessness. $Beta_2$-agonists can be short acting for immediate relief, or long acting for long term prevention of asthma symptoms.

Long acting $\beta_2$-agonists improve lung function, reduce symptoms and protect against exercise-induced dyspnea in patients with asthma and COPD. Long acting $\beta_2$-agonists induce bronchodilation by causing prolonged relaxation of airway smooth muscle. In addition to prolonged bronchodilation, long acting $\beta_2$-agonists (LABAs) exert other effects such as inhibition of airway smooth-muscle cell proliferation and inflammatory mediator release, as well as non smooth-muscle effects, such as stimulation of mucociliary transport, cytoprotection of the respiratory mucosa and attenuation of neutrophil recruitment and activation.

Further use of a long acting $\beta_2$-agonist reduces the frequency of drug administration. Currently available long acting beta$_2$-agonists (LABAs) include salmeterol and formoterol.

Even though it is known that beta$_2$-agonists provide a symptomatic relief in bronchoconstriction, another component of asthma, which is inflammation, requires separate treatment such as steroid. Most of the inhaled corticosteroids need to be administered in multiple dosage regimens.

Corticosteroids exhibit inhibitory effects on inflammatory cells and inflammatory mediators involved in the pathogenesis of respiratory disorders. Treatment with a corticosteroid/glucocorticoid is considered one of the most potent and effective therapies currently available for persistent asthma.

However, a considerable proportion of patients treated with inhaled corticosteroids (ICS) have been found to remain symptomatic, despite the use of low to moderate doses of inhaled corticosteroids (ICS).

Also, use of these corticosteroids, especially in children, has been limited due to their potential side effects. In children and teenagers, these medicines can prohibit or slow down growth and may affect the function of adrenal glands. Another possible problem in children is that these corticosteroids may cause infections such as chickenpox and measles.

Other side effects with the use of corticosteroids are that they cause suppression of the Hypothalamic-Pituitary-Adrenal (HPA) axis, produces adverse effects on the bone growth in children and on the bone density in the elderly, ocular complications (cataract formation and glaucoma) and skin atrophy. In elderly people, corticosteroids may seem to increase the risk of high blood pressure and bone diseases. Bone associated diseases by using corticosteroids are especially more likely to occur in elderly females.

Thus the therapeutic options in the treatment of asthma chronic obstructive pulmonary disease (COPD) which are not adequately controlled by the use of low to moderate doses of ICS are either to increase the dose of the inhaled corticosteroid (ICS) or to combine the therapy of an inhaled corticosteroid (ICS) with bronchodilators such as beta$_2$-agonists and/or anticholinergics.

Currently available corticosteroids include beclomethasone, budesonide, fluticasone, mometasone, ciclesonide and triamcinolone.

Anticholinergic agents also act as bronchodilators and are potential alternatives to beta agonists. However, anticholinergics can also be administered along with beta2-agonists (LABAs) for the management of asthma. Anticholinergics act by competing with acetylcholine for the receptor sites at vagus nerve or nerve-muscle junctions. This prevents the transmission of reflexes that are induced by asthma stimuli.

The use of anticholinergics provides an advantage in elderly patients as the responsiveness of β2-agonists declines with old age. Further it would be advantageous to use in patients who are intolerant to the use of beta2-agonists.

Further, anticholinergics can also be used in patients suffering from nocturnal asthma, chronic asthma with concurrent fixed way obstruction, intrinsic asthma and also in patients with asthma of longer duration.

Although a combination therapy of a bronchodilator with an inhaled corticosteroid improves pulmonary efficiency, reduces inflammatory response and provides symptomatic relief as compared to higher doses of inhaled corticosteroid alone in patients affected by respiratory disorders such as asthma, the selection of a specific bronchodilator and inhaled corticosteroid can also play a very important role in formulation of fixed dose combinations.

Additionally it simplifies the therapy, reduces the cost and also provides control of respiratory disorders. Reducing the dose frequency to the minimum is an important step in simplifying asthma management for improving patient adherence to the therapy.

Currently, there are several approved combinations of long-acting beta agonist (LABA) and inhaled corticosteroid (ICS). Some of these approved combinations for the treatment of asthma and chronic obstructive pulmonary disease (COPD) are salmeterol/fluticasone propionate (Advair diskus, Advair HFA), and formoterol fumarate dehydrate/budesonide (Symbicort).

Most of the available combinations of a long-acting beta agonist (LABA) with inhaled corticosteroid (ICS) have to be administered twice daily.

Even from the patient compliance point of view, the treatment calls for the patient to comply with different dosage regimens, different frequencies of administration, etc.

Efforts to improve compliance have been aimed at by, simplifying the medication packaging, providing effective medication reminders, improving patient education, and limiting the number of medications prescribed simultaneously.

U.S. Pat. No. 7,008,951 discloses a pharmaceutical composition comprising indacaterol and a corticosteroid for simultaneous, sequential or separate administration in the treatment of inflammatory or obstructive airway diseases and in a ratio of 100:1 to 1:300.

U.S. Pat. No. 7,622,483 discloses a combination comprising indacaterol and a steroid.

U.S. Pat. No. 6,800,643 discloses a medicament comprising separately or together indacaterol and a corticosteroid in a ratio from 100:1 to 1:300.

U.S. Pat. No. 7,622,484 discloses a composition in inhalable form comprising indacaterol and mometasone furoate for simultaneous administration in the treatment of inflammatory or obstructive airway diseases and in a ratio of 3:1 to 1:7.

U.S. Pat. No. 6,030,604 discloses a dry powder composition comprising glucocorticoids and beta-2 agonist.

WO0178745 discloses compositions containing a combination of formoterol and fluticasone propionate.

U.S. Pat. No. 7,172,752 discloses inhalation particles comprising a combination of a beta2-agonist and a glucocorticosteroid in a predetermined and constant ratio.

WO02083113 discloses pharmaceutical compositions comprising formoterol and a steroidal anti-inflammatory agent in a pharmacologically suitable fluid.

WO2004028545 discloses a combination of a long-acting beta2-agonist and a glucocorticosteroid in the treatment of fibrotic diseases.

US2005053553 discloses methods for administration by inhalation of a metered dry powder having combined doses of formoterol and fluticasone.

US2005042174 discloses a combination comprising indacaterol and of doses of a beta2-agonist, an anticholinergic agent and an anti-inflammatory steroid.

US2009088408 discloses pharmaceutical compositions of anticholinergics, corticosteroids and betamimetics and their use in the treatment of respiratory diseases.

WO2006105401 discloses anticholinergic in combination with a corticosteroid, and a long acting beta agonist, for simultaneous or sequential administration in the prevention or treatment of a respiratory, inflammatory or obstructive airway disease.

Further selecting a combination of a long-acting beta$_2$ agonist (LABA) and an inhaled corticosteroid (ICS) is critical since both drugs should be capable of being administered once daily. A treatment method where a long-acting beta$_2$ agonist (LABA) is required to be administered once daily and an inhaled corticosteroid (ICS) is required to be administered twice daily or vice versa will not be useful since the purpose of once a day treatment is defeated.

However, none of the above prior art specifically discloses the combination of indacaterol with fluticasone furoate, formoterol with fluticasone furoate or indacaterol with ciclesonide and indacaterol with fluticasone furoate and tiotropium. Moreover, none of these prior arts mention or disclose that the combination of indacaterol and fluticasone furoate, formoterol with fluticasone furoate or indacaterol with ciclesonide and indacaterol with fluticasone furoate and tiotropium can be administered once daily for the prevention or treatment of respiratory, inflammatory or obstructive airway disease.

Hence, there still remains a need to formulate a pharmaceutical composition which simplifies the dosage regimen by administering a once a day composition for the treatment of these respiratory disorders.

OBJECT OF THE INVENTION

The object of the present invention is to provide a pharmaceutical composition comprising one or more bronchodilators and one or more inhaled corticosteroid (ICS) for administration in the prevention or treatment of respiratory, inflammatory or obstructive airway disease.

Another object of the present invention is to provide a pharmaceutical composition comprising one or more bronchodilators and one or more inhaled corticosteroid (ICS) for once daily administration for the prevention or treatment of respiratory, inflammatory or obstructive airway disease.

Yet another object of the present invention is to provide a process for preparing the pharmaceutical composition comprising one or more bronchodilators and one or more inhaled corticosteroid (ICS) for administration in the prevention or treatment of respiratory, inflammatory or obstructive airway disease.

A further object of the present invention is to provide a method for prophylaxis or treatment of asthma, COPD or related a respiratory disorder which comprises administering a pharmaceutical composition comprising one or more bronchodilators and one or more inhaled corticosteroid (ICS).

SUMMARY OF THE INVENTION

According to a first aspect of the present invention, there is provided a pharmaceutical composition comprising one or more bronchodilators and one or more inhaled corticosteroid (ICS).

Preferably the composition further comprises one or more anticholinergics.

According to a second aspect of the present invention, there is provided a pharmaceutical composition comprising indacaterol and fluticasone, especially an ester of fluticasone, in particular fluticasone furoate.

According to a third aspect of the present invention, there is provided a pharmaceutical composition comprising formoterol and fluticasone, especially an ester of fluticasone, in particular fluticasone furoate.

According to a fourth aspect of the present invention, there is provided a pharmaceutical composition comprising indacaterol and ciclesonide.

According to a fifth aspect of the present invention, there is provided a pharmaceutical composition comprising indacaterol, tiotropium and fluticasone, especially an ester of fluticasone, in particular fluticasone furoate.

According to a sixth aspect of the present invention, there is provided a process for preparing the pharmaceutical compositions described above.

According to a seventh aspect of the present invention, there is provided a method for prophylaxis or treatment of asthma, COPD or a related respiratory disorder which comprises administering a pharmaceutical compositions described above.

According to a eighth aspect of the present invention there is provided the use of the pharmaceutical compositions described above in treating disorders or conditions that respond to, or are prevented, ameliorated or eliminated by, the administration of a long-acting beta agonist (LABA) and inhaled corticosteroid (ICS).

DETAILED DESCRIPTION OF THE INVENTION

Drug therapy with a bronchodilator (such as a long-acting beta agonist (LABA)) and inhaled corticosteroid (ICS) has been recommended for the prevention or treatment of respiratory, inflammatory or obstructive airway disease such as asthma and chronic obstructive pulmonary disease (COPD).

Further there is a need to formulate a composition which can be administered once daily for the prevention of conditions that respond to, or are prevented, ameliorated or eliminated by, the administration of a bronchodilator (such as a long-acting beta agonist (LABA)) and inhaled corticosteroid (ICS).

Bronchodilators used according to the present invention may be beta-agonists and/or anticholinergics. According to the present invention, beta agonists may comprise, one or more, short acting beta agonist, long acting beta agonist or ultra long acting beta agonist. In a preferred embodiment of the present invention beta agonists comprise indacaterol or formoterol.

Specific preferred pharmaceutical compositions according to the invention include:
 A corticosteroid comprising fluticasone (especially fluticasone furoate) in combination with a beta$_2$-agonist comprising formoterol.
 A corticosteroid consisting of fluticasone (especially fluticasone furoate) in combination with a beta$_2$-agonist consisting of formoterol.
 A corticosteroid comprising fluticasone (especially fluticasone furoate) in combination with a beta$_2$-agonist comprising indacaterol.
 A corticosteroid consisting of fluticasone (especially fluticasone furoate) in combination with a beta$_2$-agonist consisting of indacaterol.
 A corticosteroid comprising fluticasone (especially fluticasone furoate) in combination with a beta$_2$-agonist comprising indacaterol and an anti-cholinergic comprising tiotropium.
 A corticosteroid consisting of fluticasone (especially fluticasone furoate) in combination with a beta$_2$-agonist consisting of indacaterol and an anti-cholinergic consisting of tiotropium.
 A corticosteroid comprising ciclesonide in combination with a beta$_2$-agonist comprising indacaterol.
 A corticosteroid consisting of ciclesonide in combination with a beta$_2$-agonist consisting of indacaterol.

In an embodiment, the indacaterol is provided as the maleate.

In the above compositions, the fluticasone may be provided as the ester of fluticasone, in particular the furoate or the valerate or propionate.

The invention also encompasses methods of preparing the pharmaceutical compositions according to the invention and their use in respiratory, inflammatory or obstructive airway diseases.

It has been surprisingly found that indacaterol in combination with fluticasone furoate provides relief from respiratory disorders, while simultaneously reducing the frequency of dosage administration.

The present invention provides a novel combination for inhalation comprising indacaterol in combination with fluticasone (especially fluticasone furoate) for the prevention or treatment of respiratory, inflammatory or obstructive airway disease while simultaneously reducing the frequency of dosage administration.

Indacaterol is chemically known as (R)-5-[2-[[(5,6-Diethyl-2,3-dihydro-1H-inden-2-yl)amino]-1-hydroxyethyl]-8-hydroxyquinolin-2(1H)-one is a ultra long acting beta2-agonist. Further more indacaterol exhibits a longer duration of action.

In this specification, the terms "indacaterol", "fluticasone", "ciclesonide" and "tiotropium are used in broad sense to include not only "indacaterol" and "fluticasone" per se but also any pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs, pharmaceutically acceptable prodrugs, etc.

Fluticasone is currently available as a furoate salt and propionate salt. Fluticasone furoate is a novel corticosteroid which substantially overcomes the potential side effects that are generally produced by the use of conventional corticosteroids. Moreover fluticasone furoate exhibits a 1.7 times higher binding affinity for the human glucocorticoid receptor as compared to that of fluticasone propionate.

Fluticasone furoate has a longer duration of action with an elimination half life of 15.1 hrs. Indacaterol and formoterol have a longer duration of action of about more than 24 hrs and exhibits a faster onset of action.

We prefer that the fluticasone is provided in the form of the furoate. Fluticasone furoate is a synthetic fluorinated corticosteroid that has been developed as an intranasal treatment for patients with symptoms of rhinitis and has an enhanced affinity towards the glucocorticoid receptor.

Further, fluticasone furoate has greater potency than other clinically used corticosteroids such as mometasone furoate, budesonide, fluticasone propionate, ciclesonide for the glucocorticoid receptor and against the proinflammatory transcription factors nuclear factor κB (NF-κB), activation protein-1, and tumor necrosis factor-induced interleukin-8 cytokine production.

Fluticasone (especially fluticasone furoate) and indacaterol mainly act on two different components of asthma exhibiting a complimentary action. Chronic inflammation which is commonly associated with asthma is managed by fluticasone (especially fluticasone furoate) while other aspects of asthma, such as abnormalities in bronchial smooth muscle are improved, by indacaterol Hence, the combination of fluticasone (especially fluticasone furoate) with indacaterol provides a novel combination which has the convenience of once daily administration for patients of asthma and COPD.

Further a rapid onset of the effect of the combination due to indacaterol may increase the patient's confidence in the treatment and subsequently improve compliance to therapy.

Thus the present invention provides a pharmaceutical composition comprising indacaterol and fluticasone (especially fluticasone furoate), preferably for once daily administration.

According to another embodiment the present invention provides a pharmaceutical composition comprising indacaterol and fluticasone propionate, preferably for twice daily administration.

According to another embodiment the present invention provides a pharmaceutical composition comprising indacaterol and an ester of fluticasone, preferably for once daily administration.

Further, combination of fluticasone (especially fluticasone furoate) and indacaterol exhibits a synergistic activity, in which fluticasone furoate helps in increasing the activity of indacaterol; at the same time indacaterol helps in improving the efficacy of fluticasone furoate.

According to the present invention, indacaterol may be present in the in the amount of about 20 mcg to 1200 mcg.

According to the present invention, an ester of fluticasone may be present in the in the amount of about 0.5 mcg to 800 mcg.

According to another embodiment of the present invention the pharmaceutical composition may comprise indacaterol and fluticasone (especially fluticasone furoate) with one or more pharmaceutically acceptable excipients.

It has been surprisingly found that formoterol in combination with fluticasone (especially fluticasone furoate) provides relief form respiratory disorders, while simultaneously reducing the frequency of dosage administration.

The present invention provides a novel combination for inhalation comprising formoterol in combination with fluticasone (especially fluticasone furoate) for the prevention or treatment of respiratory, inflammatory or obstructive airway disease while simultaneously reducing the frequency of dosage administration.

Formoterol is chemically known as (±)-2-hydroxy-5-[(1RS)-1-hydroxy-2-[[(1RS)-2-(4-methoxyphenyl)-1methylethyl]-amino]ethyl]formanilide fumarate dihydrate is a selective long acting beta2-agonist. Formoterol exhibits a quick onset of action within 1-3 minutes which helps to achieve an immediate therapeutic response. Further more formoterol exhibits a longer duration of action.

Fluticasone (especially fluticasone furoate) and formoterol mainly act on two different components of asthma exhibiting a complimentary action. Chronic inflammation which is commonly associated with asthma is managed by fluticasone (especially fluticasone furoate) while other aspects of asthma, such as abnormalities in bronchial smooth muscle are improved, by formoterol.

Hence, the combination of fluticasone (especially fluticasone furoate) with formoterol provides a novel combination which has the convenience of once daily administration for patients of asthma and COPD.

Thus the present invention provides a pharmaceutical composition comprising formoterol and fluticasone (especially fluticasone furoate), preferably for once daily administration.

According to another embodiment the present invention provides a pharmaceutical composition comprising formoterol and fluticasone propionate, preferably for twice daily administration.

According to yet another embodiment the present invention provides a pharmaceutical composition comprising formoterol and an ester of fluticasone, preferably for once daily administration.

Further a rapid onset of the effect of the combination due to formoterol may increase the patient's confidence in the treatment and subsequently improve compliance to therapy.

Further, the combination of fluticasone (especially fluticasone furoate) and formoterol exhibits a synergistic activity, in which fluticasone (especially fluticasone furoate) helps in increasing the activity of formoterol; at the same time formoterol helps in improving the efficacy of fluticasone (especially fluticasone furoate).

According to the present invention, formoterol may be present in the in the amount of about 0.5 mcg to 40 mcg.

According to the present invention, an ester of fluticasone may be present in the in the amount of about 0.5 mcg to 800 mcg.

According to another embodiment of the present invention the pharmaceutical composition may comprise formoterol and fluticasone (especially fluticasone furoate) with one or more pharmaceutically acceptable excipients.

It has been surprisingly found that indacaterol in combination with ciclesonide provides relief form respiratory disorders, while simultaneously reducing the frequency of dosage administration.

The present invention also provides a novel combination for inhalation comprising indacaterol in combination with ciclesonide for the prevention or treatment of respiratory, inflammatory or obstructive airway disease while simultaneously reducing the frequency of dosage administration.

Ciclesonide, a non halogenated corticosteroid is a prodrug which is hydrolysed enzymatically by esterases in the lungs to form its active metabolite desisobutyryl ciclesonide which exhibits pronounced anti-inflammatory activity. Further ciclesonide has negligible systemic effects and therefore exhibits a better safety profile.

Ciclesonide exhibits a longer duration of action due to its lipophilic nature and lipid conjugation property. Indacaterol has a longer duration of action of about more than 24 hrs and exhibits a faster onset of action.

Ciclesonide and indacaterol mainly act on two different components of asthma exhibiting a complimentary action. Chronic inflammation which is commonly associated with asthma is managed by ciclesonide while other aspects of asthma, such as abnormalities in bronchial smooth muscle are improved, by indacaterol.

Further a rapid onset of effect of the combination due to indacaterol may increase in patient's confidence in the treatment and subsequently improve compliance to therapy.

Hence, the combination of ciclesonide with indacaterol provides a novel combination which has the convenience of once daily administration for patients of asthma and COPD.

Thus the present invention provides a pharmaceutical composition comprising indacaterol and ciclesonide, preferably for once daily administration.

Further, combination of ciclesonide and indacaterol exhibits a synergistic activity, in which ciclesonide helps in increasing the activity of indacaterol; at the same time indacaterol helps in improving the efficacy of ciclesonide.

According to the present invention, indacaterol may be present in the in the amount of about 20 mcg to 1200 mcg.

According to the present invention, ciclesonide may be present in the in the amount of about 20 mcg to 800 mcg.

According to another embodiment of the present invention the pharmaceutical composition may comprise indacaterol and ciclesonide with one or more pharmaceutically acceptable excipients.

As discussed above, the selection of a specific $\beta_2$-agonist, anticholinergic agent and inhaled corticosteroid (ICS) plays a very important role in formulation of fixed dose combinations.

We have also found that a combination therapy of fluticasone (especially fluticasone furoate), indacaterol and tiotropium is effective for the prevention or treatment of respiratory, treating inflammatory and/or obstructive airway disease such as diseases of the respiratory tract, particularly asthma and or chronic obstructive pulmonary disease (COPD).

Furthermore, the combination of fluticasone (especially fluticasone furoate), indacaterol and tiotropium provides a rapid onset of action and improved control of obstructive or inflammatory airway diseases, or reduction in the exacerbations of the diseases.

Another advantage of the combination is that the invention facilitates the treatment of an obstructive and inflammatory airway disease with a single medicament.

Further this combination therapy provides for administration of the said combination therapy by use of a single inhaler for patients who currently have to make use of multiple inhalers. This is particularly advantageous when using fluticasone furoate, which can be administered once daily along with tiotropium as compared to fluticasone propionate which is to be administered twice daily. This is particularly important in case of elderly patients who may get confused between the inhalers and who also suffer from several other medical conditions such as heart disease, arthritis etc. and are receiving multiple other medications.

Thus the present invention provides a pharmaceutical composition comprising fluticasone furoate, indacaterol and tiotropium for once daily administration.

According to another embodiment the present invention provides a pharmaceutical composition comprising fluticasone furoate, indacaterol and tiotropium for twice daily administration.

According to yet another embodiment the present invention provides a pharmaceutical composition comprising esters of fluticasone, indacaterol and tiotropium for once daily administration.

Chronic inflammation which is commonly associated with asthma is managed by fluticasone.

The anticholinergic used according to the present invention may be tiotropium. In an embodiment, the tiotropium is tiotropium bromide, especially tiotropium bromide monohydrate.

Tiotropium bromide is an anticholinergic bronchodilator that antagonises muscarinic M1, M2 and M3 receptors. Tiotropium, is chemically described as (1α, 2β, 4β, 5α, 7β)-7-[(Hydroxydi-2-thienylacetyl)oxy]-9,9-dimethyl-3-oxa-9-azoniatricyclo[3.3.1.0$^{2,4}$]nonane bromide monohydrate. Tiotropium has a longer duration of action of up to 32 hours. Also tiotropium exhibits an improvement in dyspnea and ceases the need for rescue therapy.

Tiotropium in combination with pulmonary rehabilitation (PR) associated with an increased exercise endurance time produces clinically meaningful improvements in dyspnea and health status as compared to pulmonary rehabilitation (PR alone in COPD patients.

Further, tiotropium is more potent than ipratropium in the treatment of patients with COPD in terms of the effect of lung function, dyspnea, exacerbation rates and health status.

The present invention provides a pharmaceutical composition comprising fluticasone furoate, tiotropium and indacaterol.

According to the present invention, the ester of fluticasone may be present in the in the amount of about 0.5 mcg to 800 mcg.

According to another the present invention, tiotropium may be present in the in the amount of about 2.25 mcg to 30 mcg.

According to the present invention, indacaterol may be present in the in the amount of about 20 mcg to 1200 meg.

According to one embodiment of the present invention the pharmaceutical composition may comprise indacaterol and fluticasone furoate, indacaterol and tiotropium with one or more pharmaceutically acceptable excipients.

The pharmaceutical compositions of the present invention may be administered by any suitable methods used for delivery of the drugs to the respiratory tract. The composition of the present invention may thus be administered as metered dose inhalers (MDI), dry powder inhalers (DPI), nebuliser, nasal spray, nasal drops, insufflation powders.

The various dosage forms according to the present invention may comprise one or more pharmaceutically acceptable carriers/excipients suitable for formulating the same.

The metered dose inhalers, according to the present invention may comprise one or more pharmaceutically acceptable excipients such as but not limited to HFC/HFA propellants, co-solvents, bulking agents, non volatile component, buffers/pH adjusting agents, surface active agents, preservatives, complexing agents, or combinations thereof.

Propellants are those which, when mixed with the cosolvent(s), form a homogeneous propellant system in which a therapeutically effective amount of the medicament can be dissolved. The HFC/HFA propellant must be toxicologically safe and must have a vapor pressure which is suitable to enable the medicament to be administered via a pressurized MDI.

According to the present invention the HFC/HFA propellants may comprise, one or more of 1,1,1,2-tetrafluoroethane (HFA-134(a)) and 1,1,1,2,3,3,3,-heptafluoropropane (HFA-227), difluoromethane (HFC-32), 1,1,1-trifluoroethane (HFC-143(a)), 1,1,2,2-tetrafluoroethane (HFC-134), and 1,1-difluoroethane (HFC-152a) and such other propellants which may be known to the person having a skill in the art.

Co-solvent is any solvent which is miscible in the formulation in the amount desired and which, when added provides a formulation in which the medicament can be dissolved. The function of the cosolvent is to increase the solubility of the medicament and the excipients in the formulation.

According to the present invention the co-solvent may comprise one or more of, $C_2$-$C_6$ aliphatic alcohols, such as but not limited to ethyl alcohol and isopropyl alcohol; glycols such as but not limited to propylene glycol, polyethylene glycols, polypropylene glycols, glycol ethers, and block copolymers of oxyethylene and oxypropylene; and other substances, such as but not limited to glycerol, polyoxyethylene alcohols, and polyoxyethylene fatty acid esters; hydrocarbons such as but not limited to n-propane, n-butane, isobutane, n-pentane, iso-pentane, neo-pentane, and n-hexane; and ethers such as but not limited to diethyl ether.

Suitable surfactants may be employed in the aerosol solution composition meant for administration through metered dose inhalers of the present invention which may serve to stabilize the solution formulation and improve the performance of valve systems of the metered dose inhaler.

According to the present invention the surfactant may comprise one or more ionic and/or non-ionic surfactant, but not limited to, salts of stearic acids such as magnesium stearate or esters such, as ascorbyl palmitate, isopropyl myristate and tocopherol esters oleic acid, sorbitan trioleate, lecithin, isopropylmyristate, tyloxapol, polyvinylpyrrolidone, polysorbates such as polysorbate 80, Polysorbate 20, Polysorbate 40, vitamin E-TPGS, and macrogol hydroxystearates such as macrogol-15-hydroxystearate, acetylated monoglycerides like Myvacet 9-45 and Myvacet 9-08, Polyoxyethylene ethers, ethyloleate, glyceryl trioleate, glyceryl monolaurate, glyceryl monooleate, glyceryl monosterate, glyceryl monoricinoleate, cetylalcohol, sterylalcohol, cetylpyridinium chloride, block polymers, natural oils, polyvinyl pyrrolidone, sorbitan fatty acid esters such as sorbitan trioleate, polyethoxylated sorbitan fatty acid esters (for example polyethoxylated sorbitan trioleate), sorbimacrogol oleate, synthetic amphotensides (tritons), ethylene oxide ethers of octylphenolformaldehyde condensation products, phosphatides such as lecithin, polyethoxylated fats, polyethoxylated oleotriglycerides and polyethoxylated fatty alcohols.

The surfactants may also be selected from the vast class known in the art like oils such as, but not limited to, corn oil, olive oil, cottonseed oil and sunflower seed oil, mineral oils like liquid paraffin, oleic acid and also phospholipids such as lecithin, or sorbitan fatty acid esters like sorbitan trioleate or Tween 20, Tween 60, Tween 80, PEG-25 Glyceryl trioleate, PVP, citric acid, PFDA (per fluoro-n-decanoic acid).

Non-volatile component is all the suspended or dissolved constituents that would be left after evaporation of the solvent.

According to the present invention, the non-volatile component may comprise one or more of monosaccharides such as but not limited to glucose, arabinose; disaccharides such as but not limited to lactose, maltose; oligosaccharides and polysaccharides such as but not limited to dextrans; polyalcohol such as but not limited to glycerol, sorbitol, mannitol, xylitol; salts such as but not limited to potassium chloride, magnesium chloride, magnesium sulphate, sodium chloride, sodium citrate, sodium phosphate, sodium hydrogen phosphate, sodium hydrogen carbonate, potassium citrate, potassium phosphate, potassium hydrogen phosphate, potassium hydrogen carbonate, calcium carbonate and calcium chloride.

Suitable bulking agents may be employed in metered dose inhalation composition of the present invention.

According to the present invention, the bulking agent may comprise one or more of saccharides, including monosaccharides, disaccharides, polysaccharides and sugar alcohols such as arabinose, glucose, fructose, ribose, mannose, sucrose, terhalose, lactose, maltose, starches, dextran or mannitol.

Suitable buffers or pH adjusting agents may be employed in the metered dose inhalation composition of the present invention.

According to the present invention, the buffer or the pH adjusting agent may comprise one or more of organic or inorganic acids such as, but not limited to, citric acid, ascorbic acid, hydrochloric acid, sulfuric acid, nitric acid, or phosphoric acid.

Suitable preservatives may be employed in the aerosol solution composition of the present invention to protect the formulation from contamination with pathogenic bacteria.

According to the present invention, the preservative may comprise one or more of benzalkonium chloride, benzoic acid, benzoates such as sodium benzoate and such other preservatives which may be known to the person skilled in the art.

Suitable complexing agents may be employed in the aerosol solution composition of the present invention which is capable of forming complex bonds.

According to the present invention, the complexing agent may comprise one or more of but not limited to sodium EDTA or disodium EDTA.

The pharmaceutical composition of the present invention may be administered by a dry powder inhaler (DPI).

The pharmaceutically acceptable excipients suitable for dry powder inhalation according to the present invention may be selected from suitable carriers which may comprise one or more of, but not limited to sugars such as glucose, saccharose, lactose and fructose, starches or starch derivatives, oligosaccharides such as dextrins, cyclodextrins and their derivatives, polyvinylpyrrolidone, alginic acid, tylose, silicic acid, cellulose, cellulose derivatives (for example cellulose ether), sugar alcohols such as mannitol or sorbitol, calcium carbonate, calcium phosphate, etc. lactose, lactitol, dextrates, dextrose, maltodextrin, saccharides including monosaccharides, disaccharides, polysaccharides; sugar alcohols such as arabinose, ribose, mannose, sucrose, trehalose, maltose, dextran.

The pharmaceutical composition of the present invention may be administered by nebulization.

Nebulisation therapy has an advantage over other inhalation therapy, since it is easy to use and does not require co-ordination or much effort. It also works much more rapidly than medicines taken by mouth.

For nebulisers, the composition according to the present invention may comprise suitable excipients such as tonicity agents, pH regulators, chelating agents, tonicity adjusting agents, surfactants, buffer agents in a suitable vehicle.

Isotonicity-adjusting agents, which may be used, may comprise one or more of, but not limited to, sodium chloride, potassium chloride, zinc chloride, calcium chloride and mixtures thereof. Other isotonicity-adjusting agents may also include, but are not limited to, mannitol, glycerol, and dextrose and mixtures thereof.

The pH may be adjusted by the addition of pharmacologically acceptable acids. Pharmacologically acceptable inorganic acids or organic acids may be used for this purpose. Examples of preferred inorganic acids which may be used include one or more of, but not limited to, hydrochloric acid, hydrobromic acid, nitric acid, sulphuric acid and phosphoric acid or combinations thereof. Examples of particularly suitable organic acids which may be used include one or more of, but not limited to, ascorbic acid, citric acid, malic acid, tartaric acid, maleic acid, succinic acid, fumaric acid, acetic acid, formic acid and propionic acid or combinations thereof. Examples of preferred bases which may be used include one or more of, but not limited to, aqueous ammonia solution, ammonium carbonate, sodium borate, sodium carbonate, and sodium hydroxide or combinations thereof.

Complexing/chelating agents according to the present invention may comprise one or more of, but not limited to, editic acid (EDTA) or one of the known salts thereof, e.g. sodium EDTA or disodium EDTA dihydrate (sodium edetate) or combinations thereof.

Suitable surfactants or wetting agents may also be used in the pharmaceutical compositions of the present invention. According to the present invention, surfactant may comprise one or more, but not limited to Polysorbates such as polysorbate 20, polysorbate 40, polysorbate 60, polysorbate 80, polysorbate 65, polysorbate 85, sorbitan fatty acid esters such as Span 20, Span 40, Span 60 Span 80, Span 120; sodium lauryl sulfate; polyethoxylated castor oil; polyethoxylated hydrogenated castor oil, sodium dodecyl sulfate (sodium lauryl sulfate), Lauryl dimethyl amine oxide, Docusate sodium, Cetyl trimethyl ammonium bromide (CTAB) Polyethoxylated alcohols, Polyoxyethylene sorbitan, Octoxynol, N,N-dimethyldodecylamine-N-oxide, Hexadecyltrimethylammonium bromide, Polyoxyl 10 lauryl ether, Brij, Bile salts (sodium deoxycholate, sodium cholate), Polyoxyl castor oil, Nonylphenol ethoxylate, Cyclodextrins, Lecithin, Methylbenzethonium chloride. Carboxylates, Sulphonates, Petroleum sulphonates, alkylbenzenesulphonates, Naphthalenesulphonates, Olefin sulphonates, Alkyl sulphates, Sulphates, Sulphated natural oils & fats, Sulphated esters, Sulphated alkanolamides, Alkylphenols, ethoxylated & sulphated, Ethoxylated aliphatic alcohol, polyoxyethylene surfactants, carboxylic esters Polyethylene glycol esters, Anhydrosorbitol ester & it's ethoxylated derivatives, Glycol esters of fatty acids, Carboxylic amides, Monoalkanolamine condensates, Polyoxyethylene fatty acid amides, Quaternary ammonium salts, Amines with amide linkages, Polyoxyethylene alkyl & alicyclic amines, N,N,N,N tetrakis substituted ethylenediamines 2-alkyl 1-hydroxyethyl 2-imidazolines, N-coco 3-aminopropionic acid/sodium salt, N-tallow 3-iminodipropionate disodium salt, N-carboxymethyl n dimethyl n-9 octadecenyl ammonium hydroxide, n-cocoamidethyl n-hydroxyethylglycine sodium salt etc.

According to the present invention, the buffer agents may comprise one or more of organic or inorganic acids such as but not limited to citric acid/sodium hydrogensulphate borate buffer, phosphates (sodium hydrogen orthophosphate, disodium hydrogenphosphate), trometamol, acetate buffer, citrate buffer, sodium citrate dehydrate, citric acid monohydrate, sodium dihydrogen phosphate dehydrate, anhydrous disodium hydrogen phosphate or equivalent conventional buffers.

Anti-microbial preservative agent may be added for multi-dose packages.

The composition according to the present invention may be provided in suitable containers with suitable means enabling the application of the contained formulation to the respiratory tract.

The powder for inhalation intended for administration through DPI may either be encapsulated in capsules of gelatin or HPMC or in blisters or alternatively, the dry powder may be contained as a reservoir either in a single dose or multi-dose dry powder inhalation device.

Alternatively, the powder for inhalation intended to be used for DPI may be suspended in a suitable liquid vehicle and packed in an aerosol container along with suitable propellants or mixtures thereof.

Further, the powder for inhalation intended to be used for DPI may also be dispersed in a suitable gas stream to form an aerosol composition.

The MDI composition according to the present invention may be packed in plain aluminium cans or SS (stainless steel) cans. Some aerosol drugs tend to adhere to the inner surfaces, i.e., walls of the cans and valves, of the MDI. This can lead to the patient getting significantly less than the prescribed amount of the active agent upon each activation of the MDI. Coating the inner surface of the container with a suitable polymer can reduce this adhesion problem. Suitable coatings include fluorocarbon copolymers such as FEP-PES (fluorinated ethylene propylene and polyethersulphone) and PFA-PES (perfluoroalkoxyalkane and polyethersulphone), epoxy and ethylene. Alternatively, the inner surfaces of the cans may be anodized, plasma treated or plasma coated.

It may be well acknowledged to a person skilled in the art that the said pharmaceutical composition, according to the present invention, may further comprise one or more active(s) selected from anticholinergics, antihistamines, antiallergics or leukotriene antagonist or their pharmaceutically acceptable salts, solvates, tautomers, derivatives, enantiomers, isomers, hydrates, prodrugs or polymorphs thereof.

The present invention also provides a process to manufacture the compositions according to the present invention.

The present invention provides a process of preparing a metered dose inhalation composition which process comprises admixing of a pharmaceutically acceptable carrier or excipient with the actives and the propellant and providing the composition in precrimped cans.

The present invention provides a process of preparing a dry powder inhalation composition which process comprises admixing of a pharmaceutically acceptable carrier or excipient with the actives and providing the composition to be administered through dry powder inhaler.

The present invention also provides a process of preparing an inhalation solution/suspension repulse which process comprises dissolving/dispersing the drugs, optionally chelating agents, osmotic agents and any other suitable ingredients in the vehicle and adjusting the pH using a suitable pH adjusting agent.

The present invention also provides a method for the treatment in a mammal, such as a human, for treating chronic obstructive pulmonary disease and asthma, which method comprises administration of a therapeutically effective amount of a pharmaceutical composition according to the present invention. The method of treatment may be characterized in that the pharmaceutical compositions according to the present invention are administered once a day in therapeutically effective amounts.

The present invention provides a pharmaceutical composition comprising one or more bronchodilators (such as a long-acting beta agonist (LABA)) and an inhaled corticosteroid (ICS) for use in treating disorders or conditions that respond to, or are prevented, ameliorated or eliminated by, the administration of one or more bronchodilators (such as a long-acting beta agonist (LABA)) and inhaled corticosteroid (ICS).

The following examples are for the purpose of illustration of the invention only and are not intended in any way to limit the scope of the present invention.

EXAMPLE 1

| Sr. No. | Ingredients | Qty/Spray |
| --- | --- | --- |
| 1. | Indacaterol | 50 mcg |
| 2. | Fluticasone furoate | 100 mcg |
| 3. | HFA227 | q.s. |

Process:
1) Indacaterol and Fluticasone furoate were homogenized with a part quantity of HFA.
2) The suspension obtained in step 1 was transferred to the mixing vessel where remaining quantity of HFA was added.

3) The resulting suspension was mixed, recirculated and filled in into pre-crimped aluminum cans.

EXAMPLE 2

| Sr. No. | Ingredients | Qty/Spray |
|---|---|---|
| 1. | Indacaterol | 50 mcg |
| 2. | Fluticasone fuorate | 100 mcg |
| 3. | Lactose | 100% of the drug |
| 4. | HFA227 | q.s. |

Process:
1) Indacaterol and Fluticasone furoate were homogenized with lactose and a part quantity of HFA.
2) The suspension obtained in step 1 was transferred to the mixing vessel where remaining quantity of HFA was added.
3) The resulting suspension was mixed, recirculated and filled in into pre-crimped aluminum cans.

EXAMPLE 3

| Sr. No. | Ingredients | Qty/Spray |
|---|---|---|
| 1. | Indacaterol | 50 mcg |
| 2. | Fluticasone Furoate | 100 mcg |
| 3. | PEG400/1000 | 0.3% of total formulation |
| 4. | PVP K 25 | 0.001% of total formulation |
| 5. | HFA227 | q.s. |

Process:
1) PVP was dissolved in PEG and part quantity of HFA
2) The solution obtained in Step 1 was transferred to a mixing vessel.
3) Indacaterol and Fluticasone furoate were homogenized with a part quantity of HFA.
4) The suspension obtained in step 3 was transferred to the mixing vessel where remaining quantity of HFA was added.
5) The resulting total suspension was mixed, recirculated and filled in into pre-crimped aluminum cans.

EXAMPLE 4

| Sr. No. | Ingredients | Qty/Spray |
|---|---|---|
| 1. | Indacaterol | 50 mcg |
| 2. | Fluticasone Furoate | 100 mcg |
| 3. | Ethanol | 15-20% of total formulation |
| 4. | Glycerol | 1% of total formulation |
| 5. | HCL (0.08N) | pH 2.5-3.5 |
| 6. | HFA134a | q.s. |

Process:
1) Glycerol was dissolved in ethanol and required quantity of HCl was added.
2) Indacaterol and Fluticasone furoate were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 5

| Sr. No. | Ingredients | Qty/Spray |
|---|---|---|
| 1. | Indacaterol | 50 mcg |
| 2. | Fluticasone Furoate | 100 mcg |
| 3. | Ethanol | 15-20% of total formulation |
| 4. | HCL (0.08N) | pH 2.5-3.5 |
| 5. | HFA134a | q.s. |

Process:
1) Required quantity of HCl was added to ethanol.
2) Indacaterol and Fluticasone furoate were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 6

| Sr. No. | Ingredients | Qty/Spray |
|---|---|---|
| 1. | Indacaterol | 50 mcg |
| 2. | Fluticasone Furoate | 100 mcg |
| 3. | Ethanol | 15-20% of total formulation |
| 4. | Citric acid | pH 3-4 |
| 5. | HFA134a | q.s. |

Process:
1) Required quantity of citric acid was added to ethanol.
2) Indacaterol and Fluticasone furoate were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 7

| Sr. No. | Ingredients | Qty/unit (mg) |
|---|---|---|
| 1. | Indacaterol Maleate | 0.194 |
| 2. | Fluticasone Furoate | 0.100 |
| 3. | Lactose monohydrate IP/Ph.Eur/NF | 24.7060 |
| | Total | 25.000 |

Process:
1) Indacaterol and Fluticasone furoate were sifted with a part quantity of lactose.
2) The cosift of step 1 was then sifted with the remaining quantity of lactose and blended.
3) The blend of step 2 was then filled in capsules.

EXAMPLE 8

| Sr. No. | Ingredients | Qty/unit (mg) |
|---|---|---|
| 1. | Indacaterol Maleate | 0.194 |
| 2. | Fluticasone Furoate | 0.200 |
| 3. | Lactose monohydrate IP/Ph.Eur/NF | 24.6060 |
|  | Total | 25.0000 |

Process:
1) Indacaterol and Fluticasone furoate were sifted with a part quantity of lactose.
2) The cosift of step 1 was then sifted with the remaining quantity of lactose and blended.
3) The blend of step 2 was then filled in capsules.

EXAMPLE 9

| Sr. No. | Ingredients | Qty/unit (mg) |
|---|---|---|
| 1. | Indacaterol Maleate | 0.194 |
| 2. | Fluticasone Furoate | 0.400 |
| 3. | Lactose monohydrate IP/Ph.Eur/NF | 24.4060 |
|  | Total | 25.0000 |

Process:
1) Indacaterol and Fluticasone furoate were sifted with a part quantity of lactose.
2) The cosift of step 1 was then sifted with the remaining quantity of lactose and blended.
3) The blend of step 2 was then filled in capsules.

EXAMPLE 10

| Sr. No. | Ingredients | Qty/Spray |
|---|---|---|
| 1. | Formoterol | 6 mcg |
| 2. | Fluticasone furoate | 100 mcg |
| 3. | HFA227/HFA134A | q.s. |

Process:
1) Formoterol and Fluticasone furoate were homogenized with a part quantity of HFA.
2) The suspension obtained in step 1 was transferred to the mixing vessel where remaining quantity of HFA was added.
3) The resulting suspension was mixed, recirculated and filled in into pre-crimped aluminum cans.

EXAMPLE 11

| Sr. No. | Ingredients | Qty/Spray |
|---|---|---|
| 1. | Formoterol | 6 mcg |
| 2. | Fluticasone fuorate | 100 mcg |
| 3. | Lactose | 100% of the drug |
| 4. | HFA227/HFA134A | q.s. |

Process:
1) Formoterol and Fluticasone furoate were homogenized with lactose and a part quantity of HFA.
2) The suspension obtained in step 1 was transferred to the mixing vessel where remaining quantity of HFA was added.
3) The resulting suspension was mixed, recirculated and filled in into pre-crimped aluminum cans.

EXAMPLE 12

| Sr. No. | Ingredients | Qty/Spray |
|---|---|---|
| 1. | Formoterol | 6 mcg |
| 2. | Fluticasone Furoate | 100 mcg |
| 3. | PEG400/1000 | 0.3% of total formulation |
| 4. | PVP K 25 | 0.001% of total formulation |
| 5. | HFA227/HFA134A | q.s. |

Process:
1) PVP was dissolved in PEG and part quantity of HFA
2) The solution obtained in Step 1 was transferred to a mixing vessel.
3) Formoterol and Fluticasone furoate were homogenized with a part quantity of HFA.
4) The suspension obtained in step 3 was transferred to the mixing vessel where remaining quantity of HFA was added.
5) The resulting total suspension was mixed, recirculated and filled in into pre-crimped aluminum cans.

EXAMPLE 13

| Sr. No. | Ingredients | Qty/Spray |
|---|---|---|
| 1. | Formoterol | 6 mcg |
| 2. | Fluticasone Furoate | 100 mcg |
| 3. | Ethanol | 15-20% of total formulation |
| 4. | Glycerol | 1% of total formulation |
| 5. | HCL (0.08N) | pH 2.5-3.5 |
| 6. | HFA134a/HFA134A | q.s. |

Process:
1) Glycerol was dissolved in ethanol and required quantity of HCl was added.
2) Formoterol and Fluticasone furoate were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 14

| Sr. No. | Ingredients | Qty/Spray |
|---|---|---|
| 1. | Formoterol | 6 mcg |
| 2. | Fluticasone Furoate | 100 mcg |
| 3. | Ethanol | 15-20% of total formulation |
| 4. | HCL (0.08N) | pH 2.5-3.5 |
| 5. | HFA134a/HFA134A | q.s. |

Process:
1) Required quantity of HCl was added to ethanol.
2) Formoterol and Fluticasone furoate were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 15

| Sr. No. | Ingredients | Qty/Spray |
|---|---|---|
| 1. | Formoterol | 6 mcg |
| 2. | Fluticasone Furoate | 100 mcg |
| 3. | Ethanol | 15-20% of total formulation |
| 4. | Citric acid | pH 3-4 |
| 5. | HFA134a/HFA134A | q.s. |

Process:
1) Required quantity of citric acid was added to ethanol.
2) Formoterol and Fluticasone furoate were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 16

| Sr. No. | Ingredients | Qty/Unit (mg) |
|---|---|---|
| 1. | Formoterol | 0.006 |
| 2. | Fluticasone Furoate | 0.050 |
| 3. | Lactose monohydrate IP/Ph.Eur/NF | 24.944 |
| | Total | 25.000 |

Process:
1) Sifted lactose was co-sifted with formoterol and fluticasone furoate.
2) The mixture obtained in step (1) was blended.

EXAMPLE 17

| Sr. No. | Ingredients | Qty/Unit (mg) |
|---|---|---|
| 1. | Formoterol | 0.006 |
| 2. | Fluticasone Furoate | 0.200 |
| 3. | Lactose monohydrate IP/Ph.Eur/NF | 24.794 |
| | Total | 25.000 |

Process:
1) Sifted lactose was co-sifted with formoterol and fluticasone furoate.
2) The mixture obtained in step (1) was blended.

EXAMPLE 18

| Sr. No. | Ingredients | Qty/Unit (mg) |
|---|---|---|
| 1. | Formoterol | 0.012 |
| 2. | Fluticasone Furoate | 0.400 |
| 3. | Lactose monohydrate IP/Ph.Eur/NF | 24.588 |
| | Total | 25.000 |

Process:
1) Sifted lactose was co-sifted with formoterol and fluticasone furoate.
2) The mixture obtained in step (1) was blended.

EXAMPLE 19

| Sr. No. | Ingredients | Qty/Spray |
|---|---|---|
| 1. | Indacaterol | 50 mcg |
| 2. | Ciclesonide | 100 mcg |
| 3. | HFA227 | q.s. |

Process:
1) Indacaterol and Ciclesonide were homogenized with a part quantity of HFA.
2) The suspension obtained in step 1 was transferred to the mixing vessel where remaining quantity of HFA was added.
3) The resulting suspension was mixed, recirculated and filled in into pre-crimped aluminum cans.

EXAMPLE 20

| Sr. No. | Ingredients | Qty/Spray |
|---|---|---|
| 1. | Indacaterol | 50 mcg |
| 2. | Ciclesonide | 100 mcg |
| 3. | Lactose | 100% of the drug |
| 4. | HFA227 | q.s. |

Process:
1) Indacaterol and Ciclesonide were homogenized with lactose and a part quantity of HFA.
2) The suspension obtained in step 1 was transferred to the mixing vessel where remaining quantity of HFA was added.
3) The resulting suspension was mixed, recirculated and filled in into pre-crimped aluminum cans.

EXAMPLE 21

| Sr. No. | Ingredients | Qty/Spray |
|---|---|---|
| 1. | Indacaterol | 50 mcg |
| 2. | Ciclesonide | 100 mcg |
| 3. | PEG400/1000 | 0.3% of total formulation |
| 4. | PVP K 25 | 0.001% of total formulation |
| 5. | HFA227 | q.s. |

Process:
1) PVP was dissolved in PEG and part quantity of HFA
2) The solution obtained in Step 1 was transferred to a mixing vessel.

3) Indacaterol and Ciclesonide were homogenized with a part quantity of HFA.
4) The suspension obtained in step 3 was transferred to the mixing vessel where remaining quantity of HFA was added.
5) The resulting total suspension was mixed, recirculated and filled in into pre-crimped aluminum cans.

EXAMPLE 22

| Sr. No. | Ingredients | Qty/Spray |
|---|---|---|
| 1. | Indacaterol | 50 mcg |
| 2. | Ciclesonide | 100 mcg |
| 3. | Ethanol | 15-20% of total formulation |
| 4. | Glycerol | 1% of total formulation |
| 5. | HCL (0.08N) | pH 2.5-3.5 |
| 6. | HFA134a | q.s. |

Process:
1) Glycerol was dissolved in ethanol and required quantity of HCl was added.
2) Indacaterol and Ciclesonide were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 23

| Sr. No. | Ingredients | Qty/Spray |
|---|---|---|
| 1. | Indacaterol | 50 mcg |
| 2. | Ciclesonide | 100 mcg |
| 3. | Ethanol | 15-20% of total formulation |
| 4. | HCL (0.08N) | pH 2.5-3.5 |
| 5. | HFA134a | q.s. |

Process:
1) Required quantity of HCl was added to ethanol.
2) Indacaterol and Ciclesonide were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 24

| Sr. No. | Ingredients | Qty/Spray |
|---|---|---|
| 1. | Indacaterol | 50 mcg |
| 2. | Ciclesonide | 100 mcg |
| 3. | Ethanol | 15-20% of total formulation |
| 4. | Citric acid | pH 3-4 |
| 5. | HFA134a | q.s. |

Process:
1) Required quantity of citric acid was added to ethanol.
2) Indacaterol and Ciclesonide were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 25

| Sr. No. | Ingredients | Qty/unit (mg) |
|---|---|---|
| 1. | Indacaterol Maleate | 0.194 |
| 2. | Ciclesonide | 0.100 |
| 3. | Lactose monohydrate IP/Ph.Eur/NF | 24.706 |
|  | Total | 25.000 |

Process:
1) Indacaterol and Ciclesonide were sifted with a part quantity of lactose.
2) The cosift of step 1 was then sifted with the remaining quantity of lactose and blended.
3) The blend of step 2 was then filled in capsules.

EXAMPLE 26

| Sr. No. | Ingredients | Qty/unit (mg) |
|---|---|---|
| 1. | Indacaterol Maleate | 0.194 |
| 2. | Ciclesonide | 0.200 |
| 3. | Lactose monohydrate IP/Ph.Eur/NF | 24.606 |
|  | Total | 25.000 |

Process:
1) Indacaterol and Ciclesonide were sifted with a part quantity of lactose.
2) The cosift of step 1 was then sifted with the remaining quantity of lactose and blended.
3) The blend of step 2 was then filled in capsules.

EXAMPLE 27

| Sr. No. | Ingredients | Qty/unit (mg) |
|---|---|---|
| 1. | Indacaterol Maleate | 0.194 |
| 2. | Ciclesonide | 0.400 |
| 3. | Lactose monohydrate IP/Ph.Eur/NF | 24.406 |
|  | Total | 25.000 |

Process:
1) Indacaterol and Ciclesonide were sifted with a part quantity of lactose.
2) The cosift of step 1 was then sifted with the remaining quantity of lactose and blended.
3) The blend of step 2 was then filled in capsules.

EXAMPLE 28

| Sr. No. | Ingredients | Qty/unit (mg) |
|---|---|---|
| 1. | Tiotropium bromide monohydrate | 0.0225 |
| 2. | Fluticasone Furoate | 0.100 |
| 3. | Indacaterol Maleate | 0.194 |
| 4. | Lactose monohydrate IP/Ph.Eur/NF | 24.6835 |
|  | Total | 25.000 |

Process:
1) Fluticasone furoate, Indacaterol and Tiotropium bromide were sifted with a part quantity of lactose.
2) The cosift of step 1 was then sifted with the remaining quantity of lactose and blended.
3) The blend of step 2 was then filled in capsules.

EXAMPLE 29

| Sr. No. | Ingredients | Qty/unit (mg) |
|---|---|---|
| 1. | Tiotropium bromide monohydrate | 0.0225 |
| 2. | Fluticasone Furoate | 0.200 |
| 3. | Indacaterol Maleate | 0.194 |
| 4. | Lactose monohydrate IP/Ph.Eur/NF | 24.5835 |
|  | Total | 25.0000 |

Process:
1) Fluticasone furoate, Indacaterol and Tiotropium bromide were sifted with a part quantity of lactose.
2) The cosift of step 1 was then sifted with the remaining quantity of lactose and blended.
3) The blend of step 2 was then filled in capsules.

EXAMPLE 30

| Sr. No. | Ingredients | Qty/unit (mg) |
|---|---|---|
| 1. | Tiotropium bromide monohydrate | 0.0225 |
| 2. | Fluticasone Furoate | 0.400 |
| 3. | Indacaterol Maleate | 0.194 |
| 4. | Lactose monohydrate IP/Ph.Eur/NF | 24.3835 |
|  | Total | 25.0000 |

Process:
1) Fluticasone furoate, Indacaterol and Tiotropium bromide were sifted with a part quantity of lactose.
2) The cosift of step 1 was then sifted with the remaining quantity of lactose and blended.
3) The blend of step 2 was then filled in capsules.

EXAMPLE 31

| Sr. No. | Ingredients | Qty/Spray |
|---|---|---|
| 1. | Fluticasone Furoate | 50 mcg |
| 2. | Tiotropium | 9 mcg |
| 3. | Indacaterol | 50 mcg |
| 4. | HFA134A OR HFA227 | q.s |

Process:
1) Fluticasone furoate, Indacaterol and Tiotropium were homogenized with part quantity of HFA.
2) The suspension obtained in step 1 was transferred to the mixing vessel where remaining quantity of HFA was added.
3) The resulting suspension was mixed, recirculated and filled in into pre-crimped aluminum cans.

EXAMPLE 32

| Sr. No. | Ingredients | Qty/Spray |
|---|---|---|
| 1. | Fluticasone Furoate | 50 mcg |
| 2. | Tiotropium | 9 mcg |
| 3. | Indacaterol | 50 mcg |
| 4. | Lactose | 100% of the drug |
| 5. | HFA134A OR HFA227 | q.s. |

Process:
1) Fluticasone furoate, Indacaterol and Tiotropium were homogenized with lactose and part quantity of HFA.
2) The suspension obtained in step 1 was transferred to the mixing vessel where remaining quantity of HFA was added.
3) The resulting suspension was mixed, recirculated and filled in into pre-crimped aluminum cans.

EXAMPLE 33

| Sr. No. | Ingredients | Qty/Spray |
|---|---|---|
| 1. | Fluticasone Furoate | 50 mcg |
| 2. | Tiotropium | 9 mcg |
| 3. | Indacaterol | 50 mcg |
| 4. | PEG400/1000 | 0.3% of total formulation |
| 5. | PVP K 25 | 0.001% of total formulation |
|  | HFA134A OR HFA227 | q.s. |

Process:
1) PVP was dissolved in PEG and part quantity of HFA134A or HFA227.
2) The solution obtained in Step 1 was transferred to a mixing vessel.
3) Fluticasone furoate, Indacaterol and Tiotropium were homogenized with a part quantity of HFA.
4) The suspension obtained in step 3 was transferred to the mixing vessel where remaining quantity of HFA was added.
5) The resulting total suspension was mixed, recirculated and filled in into pre-crimped aluminum cans.

EXAMPLE 34

| Sr. No. | Ingredients | Qty/Spray |
|---|---|---|
| 1. | Fluticasone Furoate | 50 mcg |
| 2. | Tiotropium | 9 mcg |
| 3. | Indacaterol | 50 mcg |
| 4. | Ethanol | 15-20% of total formulation |

-continued

| Sr. No. | Ingredients | Qty/Spray |
|---|---|---|
| 5. | Glycerol | 1% of total formulation |
| 6. | HCL (0.08N) | pH 2.5-3.5 |
| 7. | HFA134a | q.s. |

Process:

1) Glycerol was dissolved in ethanol and required quantity of HCl was added.
2) Fluticasone furoate, Indacaterol and Tiotropium were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 35

| Sr. No. | Ingredients | Qty/Spray |
|---|---|---|
| 1. | Fluticasone Furoate | 50 mcg |
| 2. | Tiotropium | 9 mcg |
| 3. | Indacaterol | 50 mcg |
| 4. | Ethanol | 15-20% of total formulation |
| 5. | HCL (0.08N) | pH 2.5-3.5 |
| 6. | HFA134a | q.s. |

Process:

1) Required quantity of HCl was added to ethanol.
2) Fluticasone furoate, Indacaterol and Tiotropium were dissolved in the solution obtained in step 1.
3) The resulting solution was transferred to the mixing vessel where HFA was added.
4) The resulting suspension was mixed, recirculated and filled in into pre-crimped aluminum cans.

EXAMPLE 36

| Sr. No. | Ingredients | Qty/Spray |
|---|---|---|
| 1. | Fluticasone Furoate | 50 mcg |
| 2. | Tiotropium | 9 mcg |
| 3. | Indacaterol | 50 mcg |
| 4. | Ethanol | 15-20% of total formulation |
| 5. | Glycerol | 1% of total formulation |
| 6. | Citric acid anhydrous | pH 2.5-3.5 |
| 7. | HFA134a | q.s. |

Process:

1) Citric acid anhydrous and glycerol were dissolved in ethanol.
2) Fluticasone furoate, Indacaterol and Tiotropium were dissolved in the solution obtained in step (1).
3) The solution obtained in step (2) was transferred to the main mixing vessel where it was mixed with entire quantity of HFA134a.
4) The resulting suspension was mixed, recirculated and filled in into pre-crimped aluminum cans.

EXAMPLE 37

| Sr. No. | Ingredients | Qty/Spray |
|---|---|---|
| 1. | Fluticasone Furoate | 50 mcg |
| 2. | Tiotropium | 9 mcg |
| 3. | Indacaterol | 50 mcg |
| 4. | Ethanol | 15-20% of total formulation |
| 5. | Citric acid anhydrous | pH 2.5-3.5 |
| 6. | HFA134a | q.s. |

Process:

1) Citric acid anhydrous was dissolved in ethanol.
2) Fluticasone furoate, Indacaterol and Tiotropium were dissolved in the solution obtained in step (1).
3) The solution obtained in step (2) was transferred to the main mixing vessel where it was mixed with entire quantity of HFA134a.
4) The resulting suspension was mixed, recirculated and filled in into pre-crimped aluminum cans.

EXAMPLE 38

| Sr. No. | Ingredients | Qty/Spray |
|---|---|---|
| 1. | Fluticasone Furoate | 50 mcg |
| 2. | Tiotropium | 9 mcg |
| 3. | Indacaterol | 50 mcg |
| 4. | Ethanol | 1-2% of total formulation |
| 5. | Lecithin | 0.02 of the API |
| 6. | HFA134a or HFA227 | q.s. |

Process:

1) Lecithin was dissolved in ethanol.
2) Tiotropium and Indacaterol were homogenized with part quantity of HFA and transferred to the mixing vessel.
3) Fluticasone furoate was homogenized with lecithin and ethanol.
4) The suspension obtained instep (3) was transferred to the main mixing vessel where the remaining quantity of HFA was added.
5) The resulting suspension was mixed, recirculated and filled in into pre-crimped aluminum cans.

EXAMPLE 39

| Sr. No. | Ingredients | Qty/Spray |
|---|---|---|
| 1. | Fluticasone Furoate | 50 mcg |
| 2. | Tiotropium | 9 mcg |
| 3. | Indacaterol | 50 mcg |
| 4. | Ethanol | 1-2% of total formulation |
| 5. | Oleic acid | 0.02-5% of the API |
| 6. | HFA134a or HFA227 | q.s. |

Process:

1) Oleic acid was dissolved in ethanol.
2) Tiotropium and Indacaterol were homogenized with part quantity of HFA and transferred to the mixing vessel.

3) Fluticasone furoate was homogenized with oleic acid and ethanol.
4) The suspension obtained instep (3) was transferred to the main mixing vessel where the remaining quantity of HFA was added.
5) The resulting suspension was mixed, recirculated and filled in into pre-crimped aluminum cans.

EXAMPLE 40

| Sr. No. | Ingredients | Qty (% w/v) |
|---|---|---|
| 1. | Formoterol Fumarate | 0.001 |
| 2. | Fluticasone Furoate | 0.025 |
| 3. | Polysorbate 80 | 0.02 |
| 4. | Sodium Chloride | 0.80 |
| 5. | Disodium Edetate | 0.01 |
| 6. | Citric acid monohydrate | 0.12 |
| 7. | Sodium Citrate Dihydrate | 0.40 |
| 8. | Sodium Hydroxide (1% w/v solution) | q.s. to pH 5.3 |
| 9. | Water For Injection | q.s. to 100 ml |

Process:
1) Sodium chloride, Disodium Edetate, Citric acid Monohydrate, Sodium Citrate dihydrate and Formoterol Fumarate were dissolved in WFI and filtered through sterilizing grade filter to obtain the main bulk.
2) Fluticasone Furoate, Polysorbate 80 & WFI were collected in a pressure vessel and subjected to sterilization by autoclave to obtain slurry.
3) The slurry obtained in step (2) was added to the main bulk obtained in step (1).
4) Weight was made up with WFI and filled in 2.0 ml in LDPE form fill seal ampoules.

EXAMPLE 41

| Sr. No. | Ingredients | Qty (% w/v) |
|---|---|---|
| 1. | Formoterol Fumarate | 0.001 |
| 2. | Fluticasone Furoate | 0.10 |
| 3. | Polysorbate 80 | 0.02 |
| 4. | Sodium Chloride | 0.80 |
| 5. | Disodium Edetate | 0.01 |
| 6. | Citric acid monohydrate | 0.12 |
| 7. | Sodium Citrate Dihydrate | 0.40 |
| 8. | Sodium Hydroxide (1% w/v solution) | q.s. to pH 5.3 |
| 9. | Water For Injection | q.s. to 100 ml |

Process:
1) Sodium chloride, Disodium Edetate, Citric acid Monohydrate, Sodium Citrate dihydrate and Formoterol Fumarate were dissolved in WFI and filtered through sterilizing grade filter to obtain the main bulk.
2) Fluticasone Furoate, Polysorbate 80 & WFI were collected in a pressure vessel and subjected to sterilization by autoclave to obtain slurry.
3) The slurry obtained in step (2) was added to the main bulk obtained in step (1).
4) Weight was made up with WFI and filled in 2.0 ml in LDPE form fill seal ampoules.

EXAMPLE 42

| Sr. No. | Ingredients | Qty (% w/v) |
|---|---|---|
| 1. | Tiotropium Bromide | 0.001 |
| 2. | Indacaterol | 0.025 |
| 3. | Fluticasone Furoate | 0.025 |
| 4. | Polysorbate 80 | 0.02 |
| 5. | Sodium Chloride | 0.90 |
| 6. | Sodium Dihydrogen Phosphate Dihydrate | 0.94 |
| 7. | Anhydrous Disodium Hydrogen Phosphate | 0.175 |
| 8. | Disodium Edetate | 0.01 |
| 9. | Water For Injection | q.s. to 100 ml |

Process:
1) Sodium chloride, Disodium Edetate, Sodium Dihydrogen Phosphate Dihydrate, Anhydrous Disodium Hydrogen Phosphate & Tiotropium Bromide were dissolved in WFI and filtered through sterilizing grade filter to obtain the main bulk.
2) Fluticasone Furoate, Indacaterol and Polysorbate 80 and WFI were collected in a pressure vessel and subjected to sterilization by autoclave to obtain slurry.
3) The slurry obtained in step (2) was added to the main bulk obtained in step (1).
4) Weight was made up with WFI and filled in 2.0 ml in LDPE form fill seal ampoules.

EXAMPLE 43

| Sr. No. | Ingredients | Qty (% w/v) |
|---|---|---|
| 1. | Tiotropium Bromide | 0.001 |
| 2. | Indacaterol | 0.05 |
| 3. | Fluticasone Furoate | 0.10 |
| 4. | Polysorbate 80 | 0.02 |
| 5. | Sodium Chloride | 0.90 |
| 6. | Sodium Dihydrogen Phosphate Dihydrate | 0.94 |
| 7. | Anhydrous Disodium Hydrogen Phosphate | 0.175 |
| 8. | Disodium Edetate | 0.01 |
| 9. | Water For Injection | q.s. to 100 ml |

Process:
1) Sodium chloride, Disodium Edetate, Sodium Dihydrogen Phosphate Dihydrate, Anhydrous Disodium Hydrogen Phosphate & Tiotropium Bromide were dissolved in WFI and filtered through sterilizing grade filter to obtain the main bulk.
2) Fluticasone Furoate, Indacaterol, Polysorbate 80 and WFI were collected in a pressure vessel and subjected to sterilization by autoclave to obtain slurry.
3) The slurry obtained in step (2) was added to the main bulk obtained in step (1).
4) Weight was made up with WFI and filled in 2.0 ml in LDPE form fill seal ampoules.

EXAMPLE 44

| Sr. No. | Ingredients | Qty (% w/v) |
|---|---|---|
| 1. | Indacaterol | 0.025 |
| 2. | Ciclesonide | 0.025 |

-continued

| Sr. No. | Ingredients | Qty (% w/v) |
|---|---|---|
| 3. | Polysorbate 80 | 0.02 |
| 4. | Sodium Chloride | 0.80 |
| 5. | Disodium Edetate | 0.01 |
| 5. | Citric Acid Monohydrate | 0.12 |
| 6. | Sodium Citrate Dihydrate | 0.40 |
| 7. | Sodium Hydroxide (1% w/v solution/ Hydrochloric acid (1N Solution) | q.s. to pH |
| 8. | Water For Injection | q.s. to 100 ml |

Process:
1) Sodium chloride, Disodium Edetate, Citric acid Monohydrate, Sodium Citrate dihydrate were dissolved in WFI and filtered through sterilizing grade filter to obtain the main bulk.
2) Indacaterol, Ciclesonide, Polysorbate 80 and WFI were collected in a pressure vessel and subjected to sterilization by autoclave to obtain slurry.
3) The slurry obtained in step (2) was added to the main bulk obtained in step (1).
4) Weight was made up with WFI and filled in 2.0 ml in LDPE form fill seal ampoules.

EXAMPLE 45

| Sr. No. | Ingredients | Qty (% w/v) |
|---|---|---|
| 1. | Indacaterol | 0.05 |
| 2. | Ciclesonide | 0.05 |
| 3. | Polysorbate 80 | 0.02 |
| 4. | Sodium Chloride | 0.80 |
| 5. | Disodium Edetate | 0.01 |
| 5. | Citric Acid Monohydrate | 0.12 |
| 6. | Sodium Citrate Dihydrate | 0.40 |
| 7. | Sodium Hydroxide (1% w/v solution/ Hydrochloric acid (1N Solution) | q.s. to pH |
| 8. | Water For Injection | q.s. to 100 ml |

Process:
1) Sodium chloride, Disodium Edetate, Citric acid Monohydrate, Sodium Citrate dihydrate were dissolved in WFI and filtered through sterilizing grade filter to obtain the main bulk.
2) Indacaterol, Ciclesonide, Polysorbate 80 and WFI were collected in a pressure vessel and subjected to sterilization by autoclave to obtain slurry.
3) The slurry obtained in step (2) was added to the main bulk obtained in step (1).
4) Weight was made up with WFI and filled in 2.0 ml in LDPE form fill seal ampoules.

EXAMPLE 46

| Sr. No. | Ingredients | Qty (% w/v) |
|---|---|---|
| 1. | Indacaterol | 0.025 |
| 2. | Fluticasone Furoate | 0.025 |
| 3. | Polysorbate 80 | 0.02 |
| 4. | Sodium Chloride | 0.90 |
| 5. | Sodium Dihydrogen Phosphate Dihydrate | 0.94 |
| 6. | Anhydrous Disodium Hydrogen Phosphate | 0.175 |
| 7. | Disodium Edetate | 0.01 |
| 8. | Water For Injection | q.s. to 100 ml |

Process:
1) Sodium chloride, Disodium Edetate, Sodium Dihydrogen Phosphate Dihydrate, Anhydrous Disodium Hydrogen Phosphate were dissolved in WFI and filtered through sterilizing grade filter to obtain the main bulk.
2) Indacaterol, Fluticasone furoate, Polysorbate 80 and WFI were collected in a pressure vessel and subjected to sterilization by autoclave to obtain slurry.
3) The slurry obtained in step (2) was added to the main bulk obtained in step (1).
4) Weight was made up with WFI and filled in 2.0 ml in LDPE form fill seal ampoules.

EXAMPLE 47

| Sr. No. | Ingredients | Qty (% w/v) |
|---|---|---|
| 1. | Indacaterol | 0.05 |
| 2. | Fluticasone Furoate | 0.10 |
| 3. | Polysorbate 80 | 0.02 |
| 4. | Sodium Chloride | 0.90 |
| 5. | Sodium Dihydrogen Phosphate Dihydrate | 0.94 |
| 6. | Anhydrous Disodium Hydrogen Phosphate | 0.175 |
| 7. | Disodium Edetate | 0.01 |
| 8. | Water For Injection | q.s. to 100 ml |

Process:
1) Sodium chloride, Disodium Edetate, Sodium Dihydrogen Phosphate Dihydrate, Anhydrous Disodium Hydrogen Phosphate were dissolved in WFI and filtered through sterilizing grade filter to obtain the main bulk.
2) Indacaterol, Fluticasone furoate, Polysorbate 80 and WFI were collected in a pressure vessel and subjected to sterilization by autoclave to obtain slurry.
3) The slurry obtained in step (2) was added to the main bulk obtained in step (1).
4) Weight was made up with WFI and filled in 2.0 ml in LDPE form fill seal ampoules.

EXAMPLE 47

| Sr. No. | Ingredients | Qty (% w/v) |
|---|---|---|
| 1. | Formoterol Fumarate | 0.001 |
| 2. | Fluticasone Propionate | 0.025 |
| 3. | Polysorbate 80 | 0.02 |
| 4. | Sodium Chloride | 0.80 |
| 5. | Disodium Edetate | 0.01 |
| 6. | Citric acid monohydrate | 0.12 |
| 7. | Sodium Citrate Dihydrate | 0.40 |
| 8. | Sodium Hydroxide (1% w/v solution) | q.s. to pH 5.3 |
| 9. | Water For Injection | q.s. to 100 ml |

Process:
1) Sodium chloride, Disodium Edetate, Citric acid Monohydrate, Sodium Citrate dihydrate and Formoterol Fumarate were dissolved in WFI and filtered through sterilizing grade filter to obtain the main bulk.
2) Fluticasone propionate, Polysorbate 80 and WFI were collected in a pressure vessel and subjected to sterilization by autoclave to obtain slurry.
3) The slurry obtained in step (2) was added to the main bulk obtained in step (1).
4) Weight was made up with WFI and filled in 2.0 ml in LDPE form fill seal ampoules.

EXAMPLE 48

| Sr. No. | Ingredients | Qty (% w/v) |
|---|---|---|
| 1. | Formoterol Fumarate | 0.001 |
| 2. | Fluticasone Propionate | 0.10 |
| 3. | Polysorbate 80 | 0.02 |
| 4. | Sodium Chloride | 0.80 |
| 5. | Disodium Edetate | 0.01 |
| 6. | Citric acid monohydrate | 0.12 |
| 7. | Sodium Citrate Dihydrate | 0.40 |
| 8. | Sodium Hydroxide (1% w/v solution) | q.s. to pH 5.3 |
| 9. | Water For Injection | q.s. to 100 ml |

Process:
1) Sodium chloride, Disodium Edetate, Citric acid Monohydrate, Sodium Citrate dihydrate and Formoterol Fumarate were dissolved in WFI and filtered through sterilizing grade filter to obtain the main bulk.
2) Fluticasone propionate, Polysorbate 80 and WFI were collected in a pressure vessel and subjected to sterilization by autoclave to obtain slurry.
3) The slurry obtained in step (2) was added to the main bulk obtained in step (1).
4) Weight was made up with WFI and filled in 2.0 ml in LDPE form fill seal ampoules.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise. Thus, for example, reference to "an excipient" includes a single excipient as well as two or more different excipients, and the like.

The invention claimed is:
1. A pressurized metered dose inhaler comprising a pharmaceutical composition consisting of:
  a) a beta2-agonist selected from indacaterol maleate in an amount ranging from 20-1200 mcg and formoterol fumarate present in an amount ranging from 0.5-40 mcg;
  b) a corticosteroid selected from fluticasone furoate in an amount ranging from 0.5-800 mcg and ciclesonide in an amount ranging from 20-800 mcg; and
  c) solubilizer selected from ethanol, PEG, glycerol, polyvinyl pyrrolidone or combination thereof; and
  d) propellant
  wherein the composition is in a form suitable for once daily administration, and
  wherein the composition further consists of a cosolvent, an antioxidant, a surfactant, a bulking agent, and a lubricant.

2. A pressurized metered dose inhaler comprising a pharmaceutical composition according to claim 1, wherein the corticosteroid is fluticasone furoate.

3. A pressurized metered dose inhaler comprising a pharmaceutical composition according to claim 1, wherein the corticosteroid is ciclesonide.

4. A pressurized metered dose inhaler comprising a pharmaceutical composition of claim 1, wherein the beta-2 agonist is indacaterol maleate and the corticosteroid is fluticasone furoate.

5. A pressurized metered dose inhaler comprising a pharmaceutical composition of claim 1, wherein the beta-2 agonist is indacaterol maleate and the corticosteroid is ciclesonide.

6. A pressurized metered dose inhaler comprising a pharmaceutical composition according to claim 1, wherein pharmaceutical composition along with any excipients are formulated in a single pharmaceutical composition.

7. A pressurized metered dose inhaler comprising a pharmaceutical composition according to claim 1, wherein the bulking agent is a saccharide and/or a sugar alcohol.

8. A pressurized metered dose inhaler comprising a pharmaceutical composition according to claim 1, further consisting of an excipient selected from a wetting agent, osmotic agent, a pH regulator, a buffering agent, and a complexing agent, provided in a pharmaceutically acceptable vehicle.

9. A method of treatment of a respiratory, inflammatory or obstructive airway disease, comprising administering a therapeutically effective amount of a pharmaceutical composition according to claim 1 to a patient in need thereof, wherein the disease is COPD or asthma.

10. A dry powder inhalation composition consisting of:
  a) indacaterol maleate in an amount ranging from 20-1200 mcg or formoterol fumarate in an amount ranging from 0.5-40 mcg;
  b) fluticasone furoate in an amount ranging from 0.5-800 mcg or ciclesonide in an amount ranging from 20-800 mcg;
  c) lactose;
  and, one or more pharmaceutically acceptable excipients selected from a propellant and a surfactant,
  wherein the composition is in a form suitable for once daily administration.

11. A method of treatment of a respiratory, inflammatory or obstructive airway disease, comprising administering a therapeutically effective amount of a composition according to claim 10 to a patient in need thereof, wherein the disease is COPD or asthma.

* * * * *